United States Patent
Pfeifer et al.

(10) Patent No.: US 11,806,464 B2
(45) Date of Patent: Nov. 7, 2023

(54) HAND-HELD SUCTION SYSTEM

(71) Applicant: Andreas Stihl AG & Co. KG, Waiblingen (DE)

(72) Inventors: Markus Pfeifer, Winnenden (DE); Jonathan Seiz, Stuttgart (DE); Alexander Fuchs, Bietigheim-Bissingen (DE); Markus Oesterle, Althuette (DE)

(73) Assignee: Andreas Stihl AG & Co. KG, Waiblingen (DE)

( * ) Notice: Subject to any disclaimer, the term of this patent is extended or adjusted under 35 U.S.C. 154(b) by 107 days.

(21) Appl. No.: 17/192,291

(22) Filed: Mar. 4, 2021

(65) Prior Publication Data
US 2021/0275731 A1    Sep. 9, 2021

(30) Foreign Application Priority Data
Mar. 5, 2020    (EP) .................................... 20161283

(51) Int. Cl.
*A61M 1/00*        (2006.01)
*A01G 20/47*       (2018.01)
(Continued)

(52) U.S. Cl.
CPC .............. *A61M 1/76* (2021.05); *A01G 20/47* (2018.02); *A47L 5/24* (2013.01); *A47L 9/1427* (2013.01); *A61M 1/63* (2021.05); *E01H 1/0836* (2013.01)

(58) Field of Classification Search
CPC . A61M 1/76; A47L 5/24; A01G 20/47; E01H 1/0836; F04D 29/007
See application file for complete search history.

(56) References Cited

U.S. PATENT DOCUMENTS

| 4,403,371 A |   | 9/1983 | Kiyooka |
| 4,870,714 A | * | 10/1989 | Miner .................. E01H 1/0809 |
|  |  |  | 15/327.5 |

(Continued)

FOREIGN PATENT DOCUMENTS

| EP | 2 617 281 A1 | 7/2013 |
| EP | 2 792 231 A1 | 10/2014 |

OTHER PUBLICATIONS

German-language European Search Report issued in European Application No. 20161283.5 dated Sep. 10, 2020 with partial English translation (eight (8) pages).

*Primary Examiner* — Eric J Rosen
*Assistant Examiner* — Christopher Soto
(74) *Attorney, Agent, or Firm* — Crowell & Moring LLP

(57) ABSTRACT

A hand-held suction system includes: a hand-held suction device, a tube unit and a bag unit, wherein the tube unit has a suction tube and a tube connecting part, and wherein the bag unit has a collecting bag and a bag connecting part. The tube connecting part and the bag connecting part are designed to form a mechanical connection to one another in order to hold the bag unit by way of the tube unit. The tube connecting part is arranged in such a way on a circumference of the suction tube, in an upper half of the circumference in a circumferential direction, in a correct operating position of the suction system, and the suction system is designed in such a way that the bag unit held by the tube unit extends downwards in the circumferential direction along the suction tube, on the upper half of the circumference.

15 Claims, 6 Drawing Sheets

(51) Int. Cl.
*A47L 5/24* (2006.01)
*A47L 9/14* (2006.01)
*E01H 1/08* (2006.01)

(56) References Cited

U.S. PATENT DOCUMENTS

| | | | | |
|---|---|---|---|---|
| 6,141,823 A | * | 11/2000 | Fujiwara | B08B 5/04 |
| | | | | 15/330 |
| 9,918,601 B2 | * | 3/2018 | Tate | A47L 9/1427 |
| 2003/0131435 A1 | * | 7/2003 | Madhat | A01G 20/47 |
| | | | | 15/327.5 |
| 2004/0221416 A1 | * | 11/2004 | Ritter | A47L 9/14 |
| | | | | 15/330 |
| 2006/0261115 A1 | * | 11/2006 | Gracer | A45F 3/04 |
| | | | | 224/653 |
| 2007/0157424 A1 | * | 7/2007 | Mottahedeh | A01G 20/47 |
| | | | | 383/103 |
| 2009/0000055 A1 | * | 1/2009 | Tate | A01G 20/47 |
| | | | | 15/330 |
| 2013/0185892 A1 | | 7/2013 | Walker | |
| 2014/0310911 A1 | | 10/2014 | Tate | |

\* cited by examiner

HAND-HELD SUCTION SYSTEM

CROSS REFERENCE TO RELATED APPLICATION

This application claims priority under 35 U.S.C. § 119 from European Patent Application No. 20161283.5, filed Mar. 5, 2020, the entire disclosure of which is herein expressly incorporated by reference.

BACKGROUND AND SUMMARY OF THE INVENTION

The invention relates to a hand-held suction system.

The problem addressed by the invention is that of providing a hand-held suction system which has improved characteristics, in particular which is more user-friendly.

The invention solves this problem by providing a hand-held suction system having the features of the independent claim. Advantageous developments and/or embodiments of the invention are described in the dependent claims.

The hand-held suction system according to the invention comprises or has a hand-held suction device, a tube unit and a bag unit. The tube unit comprises or has a suction tube and a tube connecting part, in particular just one, in particular just one single, tube connecting part. The bag unit comprises or has a collecting bag and a bag connecting part, in particular just one, in particular just one single, bag connecting part. The tube connecting part and the bag connecting part are designed or configured to form a, in particular only a, in particular only a single and/or direct, mechanical, in particular positive, connection to one another in order to hold the bag unit by means of, in particular directly by means of, the tube unit. The tube connecting part is arranged, in particular fully arranged, in such a way on a circumference of the suction tube, in an upper half of the circumference, or a half of the circumference which faces away from the ground, in a circumferential direction, in a correct operating position or alignment of the suction system, and the suction system, in particular a segment thereof, is designed or configured in such a way that the bag unit held by the tube unit extends downwards in the circumferential direction along the suction tube, on, in particular in and/or from, the upper half of the circumference, in particular in the correct operating position of the suction system.

This makes it possible for the bag unit, in particular the collecting bag, to be less in the way or not in the way of a user of the suction system, in particular it is less in the way or not in the way, in particular below the suction tube and/or the suction device, in particular in contrast to arrangement, in particular complete arrangement, of a tube connecting part on a circumference of a suction tube, at a lowermost point of the circumference in the circumferential direction in an operating position of a suction system which is not according to the invention, in particular in such a way that a bag unit held by a tube unit extends away downwards from the suction tube from the lowermost point of the circumference.

As an addition or alternative, this makes it possible for the collecting bag to exhibit or have a large volume, particularly for aspirated material, in particular it does exhibit or have such a volume, in particular in contrast to the suction system which is not according to the invention.

Thus, this allows a high degree of user-friendliness, in particular user ergonomy, of the suction system.

In particular, the hand-held suction system can be a hand-portable suction system and/or the hand-held suction device can be a hand-portable suction device. As an addition or alternative, hand-held, in particular hand-portable, suction system and/or hand-held, in particular hand-portable, suction device can mean that the suction system and/or the suction device can have a mass of at most 50 kilograms (kg), in particular of at most 20 kg, in particular of at most 10 kg, in particular of at most 5 kg, and/or of at least 1 kg, in particular of at least 2 kg, in particular without aspirated material.

The suction system can be a leaf suction system, and/or the suction device can be a leaf suction device. As an addition or alternative, the suction device can be a suction shredder. As a further addition or alternative, the suction device can have a blower fan and/or can be designed to generate a gas flow, in particular an air flow, to move aspirated material into the suction tube and through the suction tube into the collecting bag.

Particularly during correct operation of the suction system, the tube unit and the suction device can be arranged on one another for a flow of aspirated material from the suction tube to the suction device, in particular can be connected mechanically to one another, in particular directly. As an addition or alternative, particularly during the correct operation of the suction system, the tube unit and the suction device can be connected mechanically to one another, in particular directly, in order to hold the tube unit, in particular directly, by means of the suction device.

Particularly during correct operation, in particular the correct operation, of the suction system, the bag unit and the suction device can be arranged on one another for a flow of aspirated material from the suction device to the collecting bag, in particular can be connected mechanically to one another, in particular directly. As an addition or alternative, particularly during the correct operation of the suction system, the bag unit and the suction device can be connected mechanically to one another, in particular directly, in order to hold the bag unit, in particular directly, by means of the suction device.

The suction device, the tube unit and/or the bag unit can, in particular can each, be of integral design.

The suction tube and the tube connecting part can be connected to one another mechanically, in particular directly.

The collecting bag and the bag connecting part can be connected to one another mechanically, in particular directly.

The circumference may be an outer circumference.

The upper half may begin halfway and/or halfway up from the bottom upwards in the circumferential direction. As an addition or alternative, the upper half can face upwards in the operating position of the suction system.

The bag unit can touch the circumference, in particular only, in the upper half thereof.

The correct operating position can be defined by gravity or the force of gravity.

In a development of the invention, the tube connecting part is arranged in such a way, in particular in the correct operating position of the suction system, and the suction system is designed or configured in such a way that the collecting bag, in particular a segment of the collecting bag, extends along the suction tube, in particular extends downwards in the circumferential direction on the upper half of the circumference, in particular in the correct operating position of the suction system. This makes it possible for the collecting bag to exhibit or have a particularly large volume, in particular it does exhibit or have such a volume.

In a development of the invention, in the flow direction, the collecting bag extends along the suction tube for a minimum of 0.2 times, in particular a minimum of 0.3 times, in particular a minimum of 0.4 times, a length of the suction tube in the flow direction.

This makes it possible for the collecting bag to exhibit or have a particularly large volume, in particular it does exhibit or have such a volume. As an addition or alternative, this allows good, in particular aligned, holding of the bag unit, in particular of the collecting bag.

As an addition or alternative, in the flow direction, the connection extends along the suction tube for a minimum of 0.1 times, in particular a minimum of 0.15 times, in particular a minimum of 0.2 times, a length, in particular the length, of the suction tube in the flow direction.

This allows good, in particular aligned, holding of the bag unit, in particular of the collecting bag.

As a further addition or alternative, counter to the flow direction, the tube connecting part is, in particular is arranged and/or extended, a minimum of 0.2 times, in particular 0.3 times, in particular 0.4 times, a length, in particular the length, of the suction tube in the flow direction from a device-side end of the suction tube.

This makes it possible for the collecting bag to exhibit or have a particularly large volume, in particular it does exhibit or have such a volume.

In particular, in the flow direction, the collecting bag can extend along the suction tube for a maximum of 1 times, in particular a maximum of 0.8 times, in particular a maximum of 0.6 times, the length of the suction tube in the flow direction. As an addition or alternative, in the flow direction, the connection can extend along the suction tube for a maximum of 1 times, in particular a maximum of 0.6 times, in particular a maximum of 0.4 times, the length of the suction tube in the flow direction. As a further addition or alternative, counter to the flow direction, the tube connecting part can be a maximum of 1 times, in particular a maximum of 0.8 times, in particular a maximum of 0.6 times, the length of the suction tube in the flow direction from the device-side end of the suction tube. As a further addition or alternative, the flow direction can be of an aspirated material flow and/or a longitudinal direction of the suction tube. As a further addition or alternative, the suction tube can be arranged by means of the device-side end on the suction device in correct operation, in particular the correct operation, of the suction system.

In a development of the invention, the tube connecting part and the bag connecting part are designed or configured to form the connection to one another so as to allow the bag unit, in particular a segment thereof, to run optionally along, in particular either along, a left-hand half or a right-hand half of the circumference in the flow direction, in particular at the option of the user, in the operating position of the suction system. This makes it possible for the bag unit, in particular the collecting bag, to be less in the way of or not in the way of the user guiding the suction system optionally with the right hand or the left hand, in particular it is less in the way or not in the way. In particular, the tube connecting part and the bag connecting part can be designed to form the connection to one another so as to allow the bag unit to run optionally along a left-hand, upper quarter or a right-hand, upper quarter, of the circumference in the flow direction, in particular and in the circumferential direction, in the operating position of the suction system. As an addition or alternative, the left-hand half can begin halfway and/or halfway across from the right to the left in a circumferential direction. As a further addition or alternative, the left-hand half can face to the left in the operating position of the suction system. As a further addition or alternative, the right-hand half can begin halfway and/or halfway across from the left to the right in a circumferential direction. As a further addition or alternative, the right-hand half can face to the right in the operating position of the suction system. As a further addition or alternative, the left-hand half can be on one side of a plane extending from the top down and from the front to the rear, in particular in the flow direction and/or through a longitudinal axis of the suction tube, in the operating position of the suction system, and the right-hand half can be on an opposite side of the plane. As a further addition or alternative, the bag unit can touch the circumference, in particular only, in either its left-hand half or right-hand half, in particular in its upper left-hand quarter or its upper right-hand quarter.

In a development of the invention, the tube connecting part is arranged, in particular completely, at an uppermost point of the circumference in a circumferential direction in the operating position of the suction system. This makes it possible for the bag unit to extend optionally on the left-hand half or the right-hand half of the circumference in the flow direction, in the operating position of the suction system.

In a development of the invention, the tube connecting part comprises or has a loop hanger arrangement, in particular the tube connecting part is a loop hanger arrangement. In addition or as an alternative, the bag connecting part comprises or has a loop, in particular the bag connecting part is a loop. This allows the connection to be produced easily. In addition or as an alternative, this makes it possible for the bag unit to extend optionally on the left-hand half or the right-hand half of the circumference in the flow direction, in the operating position of the suction system. In particular, the loop can be arranged with its ends on the collecting bag.

In a development of the invention, the suction system is designed or configured to form an arrangement, in particular a mechanical connection, of the bag unit on, in particular with, the suction device and the tube unit which can be released, in particular without tools and/or without destruction. In addition or as an alternative, the suction system is designed or configured to form an arrangement, in particular a mechanical connection, of the tube unit on, in particular with, the suction device and the bag unit which can be released, in particular without tools and/or without destruction. This allows easy transportation and/or space-saving storage of the bag unit and/or of the tube unit, in particular of the suction system. As an addition or alternative, this allows easy emptying of the bag unit, in particular of the collecting bag. In particular, the bag unit and/or the tube unit can, in particular can each, be referred to as attachments.

In one embodiment of the invention, the loop is designed or configured as a carrying handle to enable the released bag unit to be carried by a user, in particular the user. This allows multi-functionality of the loop.

In one embodiment of the invention, the collecting bag comprises or has a resealable emptying aperture, in particular for emptying aspirated material. The loop and the emptying aperture are arranged in such a way relative to one another that the emptying aperture of the collecting bag is not oriented or facing downwards when the released bag unit is being carried, or owing to its being carried, by, in particular only by, the loop. This makes it possible to avoid or even prevent a risk of unintended emptying of the collecting bag while it is being carried. In particular, the emptying aperture of the collecting bag can be oriented upwards while it is being carried. In addition or as an alternative, the collecting bag can be aligned by gravity or the force of gravity while it is being carried.

In a development of the invention, the collecting bag comprises or has a, in particular the, resealable emptying aperture, and/or an emptying aperture that can be resealed by means of a zip fastener, in particular for emptying aspirated material. The collecting bag comprises or has a backing, at least in an end region of the emptying aperture. This makes it possible to avoid or even prevent a risk of unintended emptying of the collecting bag when the emptying aperture is not fully closed. In particular, the backing can have, in particular can be, a sealing layer, in particular made of textile.

In a development of the invention, a shape of the collecting bag is not mirror-symmetrical with respect to a, in particular arbitrary or freely selectable, plane extending from the top down and from the front to the rear, in particular in the flow direction, in the operating position of the suction system, in particular is not mirror-symmetrical, irrespective of the optional extent of the bag unit on the left-hand half or the right-hand half of the circumference in the flow direction in the operating position of the suction system, where present.

This makes it possible for the bag unit, in particular the collecting bag, to be less in the way of or not in the way of the user guiding the suction system with, in particular either, the right hand or the left hand, in particular it is less in the way or not in the way.

In addition or as an alternative, a gas permeability of the collecting bag is not mirror-symmetrical with respect to a, in particular arbitrary or freely selectable, and/or the, plane extending from the top down and from the front to the rear, in particular in the flow direction, in the operating position of the suction system, in particular is not mirror-symmetrical, irrespective of the optional extent of the bag unit on the left-hand half or the right-hand half of the circumference in the flow direction in the operating position of the suction system, where present.

This makes it possible for there to be less of an air flow or no air flow towards the user guiding the suction system with, in particular either, the right hand or the left hand, in particular there is less or no such air flow.

In particular, the collecting bag can have a gas-permeable textile.

In a development of the invention, the tube unit is designed or configured to form an arrangement, in particular the arrangement, in particular is arranged, on a tube side of the suction device, in particular on the suction device and/or completely. The bag unit is designed or configured to form an arrangement, in particular the arrangement, in particular is arranged, on a bag side of the suction device which is different from the tube side, in particular a side facing away therefrom, in particular being formed or configured on the suction device and/or at least partially. This allows a good balance of the suction system and/or a good flow profile in the suction device. In particular, an angle between a line orthogonal or normal to the tube side and a line orthogonal or normal to the bag side can be at least 75 degrees (°) and/or at most 165°, in particular 90°. In addition or as an alternative, the tube connecting part can be arranged on a side of the circumference of the suction tube facing away from, in particular opposite to, the bag side or the arrangement of the bag unit on the suction device.

In one embodiment of the invention, the tube side, in particular a line orthogonal or normal to the tube side, faces or is aligned forwards and downwards, in particular counter to the flow direction, in the operating position of the suction system. The suction side, in particular a line orthogonal or normal to the suction side, faces or is aligned rearwards, in particular and downwards, in the operating position of the suction system.

In a development of the invention, the suction device comprises or has a handle, in particular at least one handle, for a, in particular the, user for the purpose of guiding, in particular and carrying, the suction system. The handle is arranged, in particular fully arranged, on the top of the suction device in the operating position of the suction system. This allows easy guidance, in particular carrying, of the suction system. In particular, the suction system can be aligned into the operating position, in particular by gravity or the force of gravity, during and/or owing to the carrying of the suction device, in particular by the at least one handle, in particular only by the at least one handle.

In a development of the invention, the suction tube has or exhibits a round, in particular circular, cross section at the tube connecting part. This allows simple production of the suction tube and/or a low flow resistance of the suction tube. In particular, the cross section can be orthogonal or normal to the flow direction. In addition or as an alternative, the suction tube can exhibit or have an elliptical cross section.

Further advantages and aspects of the invention will become apparent from the claims and from the following description of preferred exemplary embodiments of the invention, which are explained below with reference to the drawings.

DETAILED DESCRIPTION OF THE DRAWINGS

Figure 1:
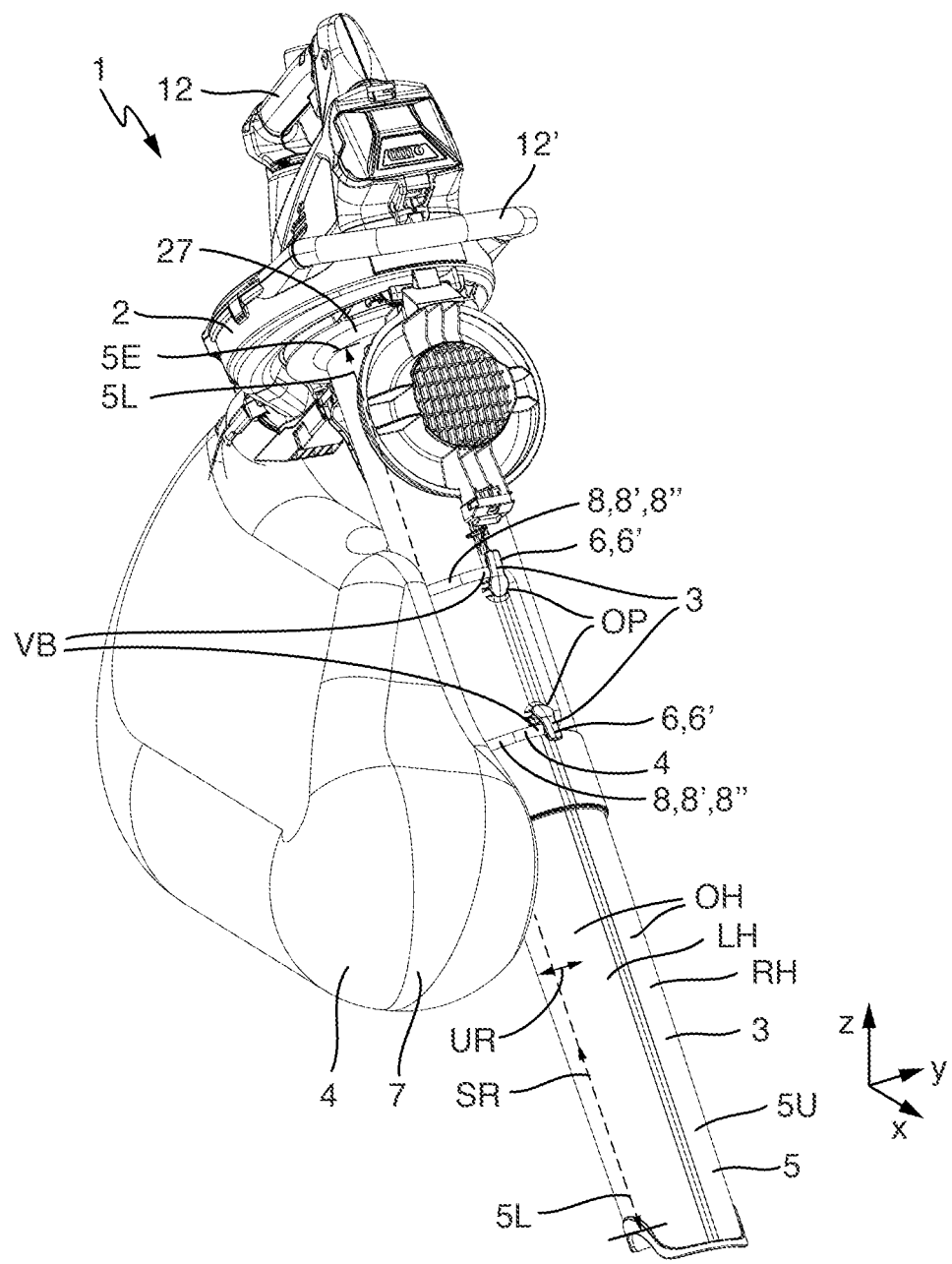
FIG. 1 shows a perspective view of an exemplary hand-held suction system according to the invention from the front right.

FIGS. 1 to 4 show a hand-held suction system 1. The suction system 1 has a hand-held suction device 2, a tube unit 3 and a bag unit 4. The tube unit 3 has a suction tube 5 and a tube connecting part 6. The bag unit 4 has a collecting bag 7 and a bag connecting part 8. The tube connecting part 6 and the bag connecting part 8 are designed to form a mechanical connection VB to one another in order to hold the bag unit 4 by means of the tube unit 3, in particular the tube connecting part 6 and the bag connecting part 8 are connected mechanically to one another. The tube connecting part 6 is arranged in such a way on a circumference 5U of the suction tube 5, in an upper half OH of the circumference 5U in a circumferential direction UR, in a correct operating position of the suction system 1, and the suction system 1 is designed in such a way that the bag unit 4 held by the tube unit 3 extends downwards in the circumferential direction UR along the suction tube 5, on the upper half OH of the circumference 5U.

In detail, the tube connecting part 6 is arranged in such a way, and the suction system 1 is designed in such a way that the collecting bag 7 extends along the suction tube 5, in particular extends downwards in the circumferential direction UR on the upper half OH of the circumference 5U, as shown in FIG. 1.

Figure 3:
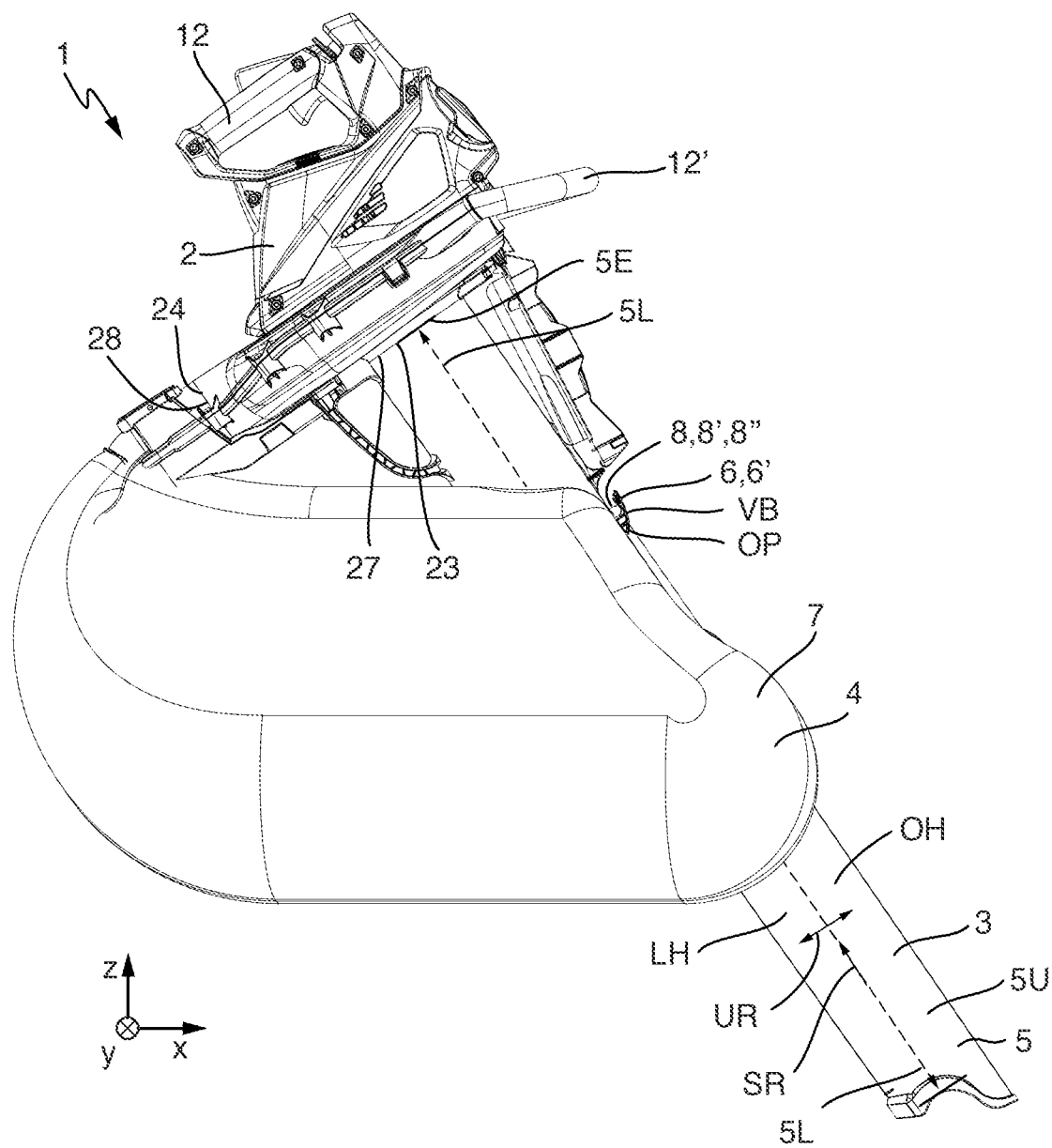
FIG. 3 shows another perspective view of the suction system of FIG. 1 from the right.

Furthermore, in the flow direction SR, in particular in the −xz direction, the collecting bag 7 extends along the suction tube 5 for a minimum of 0.2 times, in particular a minimum of 0.3 times, in particular a minimum of 0.4 times, a length 5L of the suction tube 5 in the flow direction SR, as shown in FIG. 3.

Figure 2:
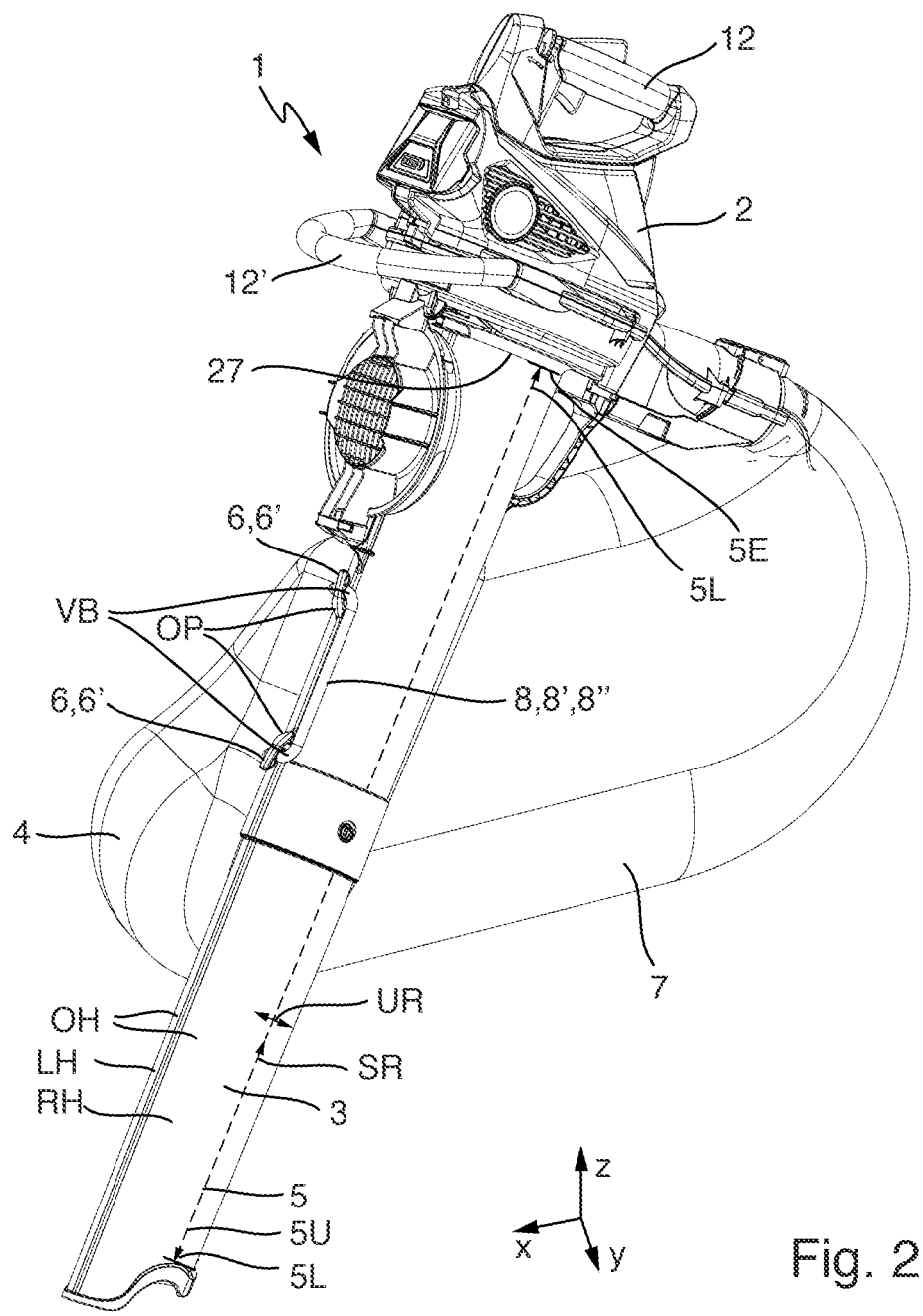
FIG. 2 shows another perspective view of the suction system of FIG. 1 from the front left.

In addition, in the flow direction SR, the connection VB extends along the suction tube 5 for a minimum of 0.1 times, in particular a minimum of 0.15 times, in particular a minimum of 0.2 times, the length 5L of the suction tube 5 in the flow direction SR, as shown in FIGS. 1 and 2.

As a further addition, counter to the flow direction SR, the tube connecting part 6 is, in particular is arranged and/or extended, a minimum of 0.2 times, in particular 0.3 times, in particular 0.4 times, the length 5L of the suction tube 5 in the flow direction SR from a device-side end 5E of the suction tube 5, as shown in FIGS. 1 to 3.

Moreover, the tube connecting part 6 and the bag connecting part 8 are designed to form the connection VB to one another so as to allow the bag unit 4 to run optionally along a left-hand half LH, as shown in FIGS. 1 to 4, or a right-hand half RH of the circumference 5 in the flow direction SR in the operating position of the suction system 1.

Furthermore, the tube connecting part 6 is arranged at an uppermost point OP of the circumference 5 in a circumferential direction UR in the operating position of the suction system 1.

Moreover, the tube connecting part 6 has a loop hanger arrangement 6', in particular the tube connecting part 6 is a loop hanger arrangement 6'.

In addition, the bag connecting part 8 has a loop 8', in particular the bag connecting part 8 is a loop 8'.

In other words: the tube connecting part 6 and the bag connecting part 8 are such that the bag connecting part 8 is suspended asymmetrically on the symmetrical tube connecting part 6.

Furthermore, the suction system 1 is designed to form an arrangement of the bag unit 4 on the suction device 2 and the tube unit 3 which can be released, in particular without tools.

In addition, the suction system 1 is designed to form an arrangement of the tube unit 3 on the suction device 2 and the bag unit 4 which can be released, in particular without tools.

In FIGS. 1 to 4, the bag unit 4 is arranged on the suction device 2 and the tube unit 3. In addition, the tube unit 3 is arranged on the suction device 2 and the bag unit 4.

Figure 5:
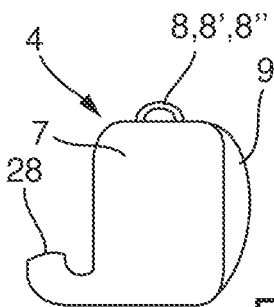
FIG. 5 shows a view of a bag unit of the suction system of FIG. 1 while being carried.
Figure 8:
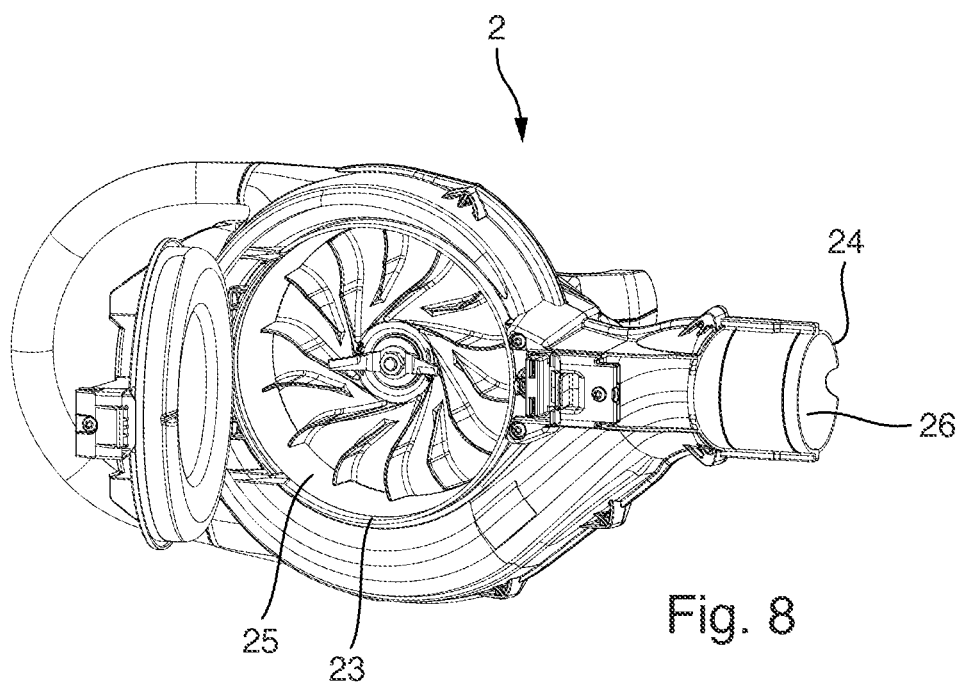
FIG. 8 shows a view of a suction device of the suction system of FIG. 1.

In FIGS. 5 and 8, the bag unit 4 has been released from the suction device 2 and the tube unit 3.

Figure 7:
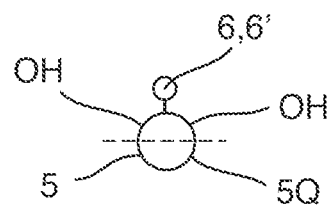
FIG. 7 shows a cross-sectional view of a tube unit of the suction system of FIG. 1.

In FIGS. 7 and 8, the tube unit 3 has been released from the suction device 2 and the bag unit 4.

In detail, the loop 8' is designed as a carrying handle 8" to enable the released bag unit 4 to be carried by a user.

Figure 6:
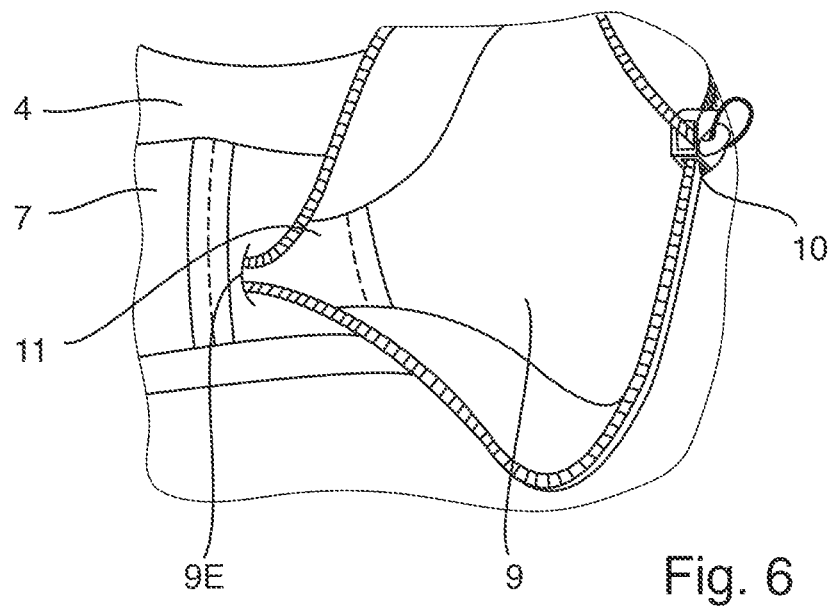
FIG. 6 shows a view of a backing of an emptying aperture of a collecting bag of the bag unit of FIG. 5.

Moreover, the collecting bag 7 has a resealable emptying aperture 9, in particular an emptying aperture that can be resealed by means of a zip fastener 10, as shown in FIGS. 5 and 6.

The loop 8' and the emptying aperture 9 are arranged in such a way relative to one another that the emptying aperture 9 of the collecting bag 7 is not oriented downwards when the released bag unit 4 is being carried by the loop 8', as shown in FIG. 5.

Furthermore, the collecting bag 7 has a backing 11, at least in an end region 9E of the emptying aperture 9, as shown in FIG. 6.

Figure 4:
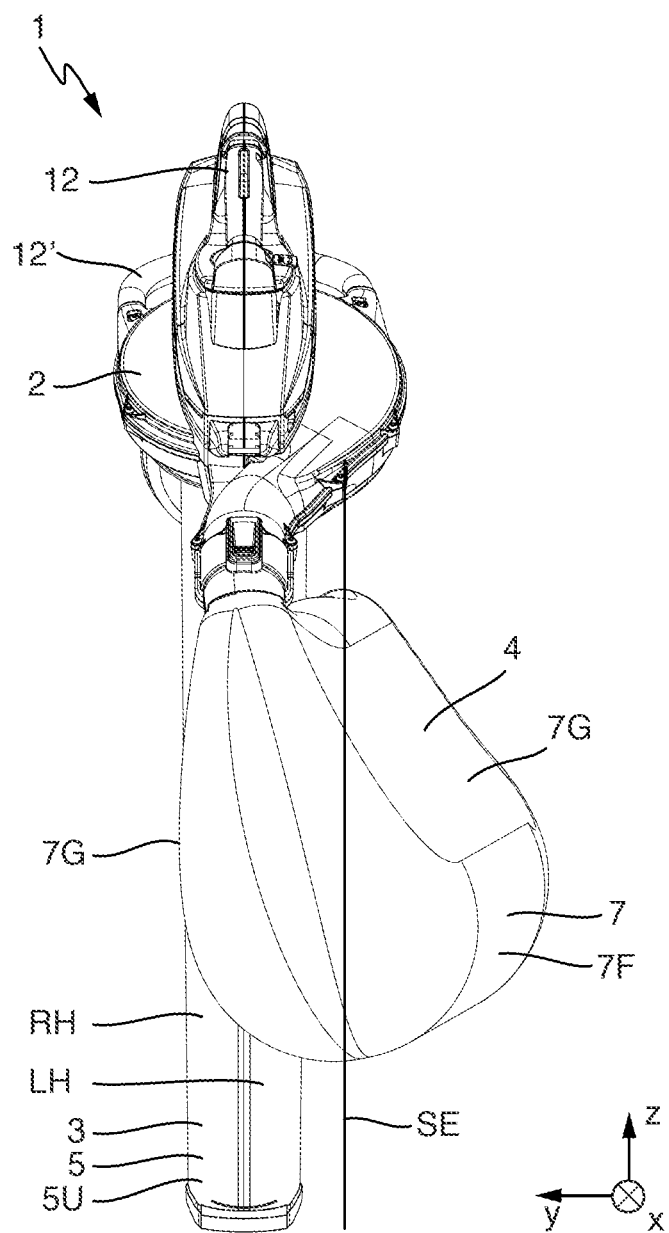
FIG. 4 shows another perspective view of the suction system of FIG. 1 from the rear.

Moreover, a shape 7F of the collecting bag 7 is not mirror-symmetrical with respect to a plane SE extending from the top down, in particular in the −z direction, and from the front to the rear, in particular in the −x direction, in the operating position of the suction system 1, as shown in FIG. 4. In other words: the collecting bag 7 is of asymmetrical construction.

In the exemplary embodiment shown, this makes it possible for the bag unit 4, in particular the collecting bag 7, to be less in the way of or not in the way of the user guiding the suction system 1 with the right hand, in particular it is less in the way or not in the way.

In alternative exemplary embodiments, the shape of the collecting bag may not be mirror-symmetrical with respect to the plane extending from the top downwards and from the front to the rear in the operating position of the suction system, thus making it possible to enable the bag unit, in particular the collecting bag, to be less in the way or not in the way of the user guiding the suction system with the left hand, in particular said unit being less in the way or not in the way.

In addition, a gas permeability 7G of the collecting bag 7 is not mirror-symmetrical with respect to the plane SE extending from the top down and from the front to the rear in the operating position of the suction system 1, as shown in FIG. 4.

In the exemplary embodiment shown, this makes it possible for there to be less of an air flow or no air flow towards the user guiding the suction system 1 with the right hand, in particular there is less or no such air flow. In other words: the gas permeability 7G of the collecting bag 7 is greater in the −y direction than in the y direction. In yet other words: gas-permeable regions are installed on the collecting bag 7 in such a way that gas is directed primarily away from the user.

In alternative exemplary embodiments, the gas permeability of the collecting bag may not be mirror-symmetrical with respect to the plane extending from the top downwards and from the front to the rear in the operating position of the suction system, thus making it possible to enable less of an air flow or no air flow to flow towards the user guiding the suction system with the left hand, in particular there is less or no such air flow.

Furthermore, the tube unit 3 is designed to form the arrangement, in particular is arranged, on a tube side 23 of the suction device 2. The bag unit 4 is designed to form the arrangement, in particular is arranged, on a bag side 24 of the suction device 2 which is different from the tube side 23, in particular a side facing away therefrom.

In detail, the tube side 23 faces forwards and downwards, in particular in the x-z direction, in the operating position of the suction system 1, as shown in FIGS. 1 to 4. The suction side 24 faces rearwards, in particular in the −x direction, in particular and downwards, in particular in the −z direction, in the operating position of the suction system 1.

In particular, the suction device 2 has a tube connecting aperture 25, as shown in FIG. 8. The tube unit 3, in particular the suction tube 5, has a tubular-device connecting aperture 27. With the tubular-device connecting aperture 27, the tube unit 3 is designed to form the arrangement, in particular is arranged, on the tube connecting aperture 25 of the suction device 2.

Moreover, the suction device 2 has a bag connecting aperture 26, as shown in FIG. 8. The bag unit 4, in particular the collecting bag 7, has a bag-device connecting aperture 28. With the bag-device connecting aperture 28, the bag unit 4 is designed to form the arrangement, in particular is arranged, on the bag connecting aperture 26 of the suction device 2.

Furthermore, the suction device 2 has a handle 12 for the user for guiding the suction system 1. The handle 12 is arranged on the top of the suction device 2 in the operating position of the suction system 1.

In the exemplary embodiment shown, the suction device 2 has a further handle 12'.

Moreover, the suction tube 5 has a round, in particular circular, cross section 5Q at the tube connecting part 6, as shown in FIG. 7.

As the exemplary embodiments shown and described above make clear, the invention provides a hand-held suction system which has improved characteristics, in particular is more user-friendly.

What is claimed is:

1. A hand-held suction system, comprising:
a hand-held suction device;
a tube unit; and
a bag unit,
wherein the tube unit has a suction tube and a tube connecting part,
wherein the bag unit has a collecting bag and a bag connecting part,
wherein the tube connecting part and the bag connecting part are designed to form a mechanical connection to one another in order to hold the bag unit by way of the tube unit,
wherein the tube connecting part is arranged in such a way on a circumference of the suction tube, in an upper half of the circumference in a circumferential direction, in an operating position of the suction system, and the suction system is designed such that the bag unit held by the tube unit via the tube connecting part mechanically connecting with the bag connecting part extends downwards in the circumferential direction along the suction tube, on the upper half of the circumference, wherein the upper half faces upwards in the operating position of the suction system.

2. The hand-held suction system according to claim 1, wherein at least one of:
in a flow direction, the collecting bag extends along the suction tube for a minimum of 0.2 times a length of the suction tube in the flow direction,
in the flow direction, the connection extends along the suction tube for a minimum of 0.1 times a length of the suction tube in the flow direction, or
counter to the flow direction, the tube connecting part is a minimum of 0.2 times a length of the suction tube in the flow direction from a device-side end of the suction tube.

3. The hand-held suction system according to claim 1, wherein the tube connecting part and the bag connecting part are designed to form the connection to one another so as to allow the bag unit to run optionally along a left-hand half or a right-hand half of the circumference in a flow direction in the operating position of the suction system.

4. The hand-held suction system according to claim 1, wherein the tube connecting part is arranged at an uppermost point of the circumference in a circumferential direction in the operating position of the suction system.

5. The hand-held suction system according to claim 1, wherein the tube connecting part is a loop hanger arrangement, and/or
wherein the bag connecting part is a loop.

6. The hand-held suction system according to claim 5, wherein the loop is designed as a carrying handle to enable a released bag unit to be carried by a user.

7. The hand-held suction system according to claim 6, wherein the collecting bag has a resealable emptying aperture,
wherein the loop and the emptying aperture are arranged relative to one another such that the emptying aperture of the collecting bag is not oriented downwards when the released bag unit is being carried by the loop.

8. The hand-held suction system according to claim 1, wherein the suction system is designed to form an arrangement of the bag unit on the suction device and the tube unit which is releasable without tools, and/or
wherein the suction system is designed to form an arrangement of the tube unit on the suction device and the bag unit which is releasable without tools.

9. The hand-held suction system according to claim 1, wherein the collecting bag has an emptying aperture that is resealable via a zip fastener,
wherein the collecting bag has a backing, at least in an end region of the emptying aperture.

10. The hand-held suction system according to claim 1, wherein a shape of the collecting bag is not mirror-symmetrical with respect to a plane extending from the top down and from the front to the rear in the operating position of the suction system, and/or
wherein a gas permeability of the collecting bag is not mirror-symmetrical with respect to a plane extending from the top down and from the front to the rear in the operating position of the suction system.

11. The hand-held suction system according to claim 1, wherein the tube unit is arranged on a tube side of the suction device, and
wherein the bag unit is arranged on a bag side of the suction device which is different from the tube side.

12. The hand-held suction system according to claim 11, wherein the tube side faces forwards and downwards in the operating position of the suction system, and
wherein the bag side faces rearwards and downwards in the operating position of the suction system.

13. The hand-held suction system according to claim 1, wherein the suction device has a handle for a user for guiding the suction system,
wherein the handle is arranged on the top of the suction device in the operating position of the suction system.

14. The hand-held suction system according to claim 1, wherein the suction tube has a circular cross section at the tube connecting part.

15. A hand-held suction system, comprising:
a hand-held suction device;
a tube unit; and
a bag unit, wherein the tube unit has a suction tube and a tube connecting part,
wherein the bag unit has a collecting bag and a bag connecting part, wherein the tube connecting part and the bag connecting part are designed to form a mechanical connection to one another in order to hold the bag unit by way of the tube unit, wherein the tube connecting part is arranged in such a way on a circumference of the suction tube, in an upper half of the circumference in a circumferential direction, in an operating position of the suction system, and the suction system is designed such that the bag unit held by the tube unit extends downwards in the circumferential direction along the suction tube, on the upper half of the circumference, wherein the tube connecting part is arranged in such a way and the suction system is designed in such a way that the collecting bag extends along and touches the suction tube downwards in the circumferential direction on the upper half of the circumference.

\* \* \* \* \*